United States Patent
You et al.

(10) Patent No.: US 10,646,424 B2
(45) Date of Patent: May 12, 2020

(54) ORAL COMPOSITION

(71) Applicant: LG HOUSEHOLD & HEALTH CARE LTD., Seoul (KR)

(72) Inventors: Aram You, Daejeon (KR); Kyo-Tae Moon, Daejeon (KR); Won-Ho Ha, Daejeon (KR); In-Ho Lee, Daejeon (KR)

(73) Assignee: LG Household & Health Care Ltd. (KR)

(*) Notice: Subject to any disclaimer, the term of this patent is extended or adjusted under 35 U.S.C. 154(b) by 0 days.

(21) Appl. No.: 14/899,408

(22) PCT Filed: Jun. 18, 2014

(86) PCT No.: PCT/KR2014/005384
§ 371 (c)(1),
(2) Date: Dec. 17, 2015

(87) PCT Pub. No.: WO2014/204221
PCT Pub. Date: Dec. 24, 2014

(65) Prior Publication Data
US 2016/0151255 A1    Jun. 2, 2016

(30) Foreign Application Priority Data

Jun. 18, 2013 (KR) .................. 10-2013-0069581
Jun. 18, 2013 (KR) .................. 10-2013-0069582
Jun. 18, 2013 (KR) .................. 10-2013-0069583
Jun. 18, 2013 (KR) .................. 10-2013-0069584
Oct. 11, 2013 (KR) .................. 10-2013-0121397
Oct. 11, 2013 (KR) .................. 10-2013-0121408
Oct. 11, 2013 (KR) .................. 10-2013-0121417
Oct. 11, 2013 (KR) .................. 10-2013-0121432
Oct. 18, 2013 (KR) .................. 10-2013-0124515

(51) Int. Cl.
| *A61K 8/34* | (2006.01) |
| *A61Q 11/00* | (2006.01) |
| *A61K 8/04* | (2006.01) |
| *A61K 8/21* | (2006.01) |
| *A61K 8/73* | (2006.01) |
| *A61K 8/25* | (2006.01) |
| *A61K 8/37* | (2006.01) |
| *A61K 8/46* | (2006.01) |
| *A61K 8/49* | (2006.01) |
| *A61K 8/19* | (2006.01) |
| *A61K 8/24* | (2006.01) |
| *A61K 8/81* | (2006.01) |
| *A61K 8/86* | (2006.01) |

(52) U.S. Cl.
CPC .............. *A61K 8/345* (2013.01); *A61K 8/042* (2013.01); *A61K 8/19* (2013.01); *A61K 8/24* (2013.01); *A61K 8/25* (2013.01); *A61K 8/73* (2013.01); *A61K 8/731* (2013.01); *A61K 8/8147* (2013.01); *A61K 8/86* (2013.01); *A61Q 11/00* (2013.01); *A61K 2800/48* (2013.01); *A61K 2800/5922* (2013.01); *A61K 2800/87* (2013.01)

(58) Field of Classification Search
CPC . A61K 8/345; A61K 8/21; A61K 8/37; A61K 8/042; A61K 8/73; A61K 8/25; A61K 8/463; A61K 8/19; A61K 8/24; A61K 8/49; A61K 8/678; A61K 2800/48; A61K 2800/5922; A61Q 11/00
See application file for complete search history.

(56) References Cited

U.S. PATENT DOCUMENTS

| 4,664,907 | A | * | 5/1987 | Muller | ................... | A61Q 11/00 424/49 |
| 4,830,221 | A | * | 5/1989 | Mazzanobile | ......... | A61Q 11/00 222/260 |
| 4,961,924 | A | * | 10/1990 | Suhonen | ................... | A61K 8/21 424/52 |
| 5,178,869 | A | * | 1/1993 | Ebine | ................... | A61K 8/4926 222/192 |
| 6,042,812 | A | * | 3/2000 | Sanker | ..................... | A61K 8/21 424/49 |

(Continued)

FOREIGN PATENT DOCUMENTS

| JP | H04270210 A | 9/1992 |
| JP | 2006501044 A | 1/2006 |

(Continued)

OTHER PUBLICATIONS

Toagosei (2007). Rheogic. *Technical Information* pp. 1-6.
International Search Report (ISR) dated Oct. 28, 2014 in PCT/KR2014/005384.

*Primary Examiner* — Lezah Roberts
(74) *Attorney, Agent, or Firm* — Lerner, David, Littenberg, Krumholz & Mentlik, LLP

(57) ABSTRACT

Provided is a pumping type toothpaste product including a toothpaste composition. The toothpaste composition includes a polishing agent, and thus prevents the piston of a pumping type container from being worn by the polishing agent contained in the toothpaste composition so that the contents of the container may be ejected out smoothly. Also provided is a gel-like toothpaste composition having excellent viscosity retentivity. Further, provided is an oral composition showing high elasticity even at low viscosity, undergoing little change in viscosity with time and having significantly improved shape retentivity, flowability and dispersion stability through the synergic effect of xanthan gum and a thickening polymer.

7 Claims, 4 Drawing Sheets

(56) References Cited

U.S. PATENT DOCUMENTS

| | | | |
|---|---|---|---|
| 8,337,818 B2 | 12/2012 | Lin et al. | 424/49 |
| 2005/0089481 A1* | 4/2005 | Yamanaka | A61K 8/24 424/50 |
| 2010/0297198 A1 | 11/2010 | Kim | 424/401 |
| 2012/0004303 A1* | 1/2012 | Benson | A61K 9/006 514/535 |

FOREIGN PATENT DOCUMENTS

| | | | | |
|---|---|---|---|---|
| JP | 2007-001954 A | 1/2007 | | |
| JP | 2009-215176 | 9/2009 | | A61K 8/34 |
| KR | 10-2001-0075492 | 8/2001 | | A61K 8/03 |
| KR | 10-2004-0021851 | 3/2004 | | A61K 8/25 |
| KR | 10-2005-0048853 A | 5/2005 | | A61K 8/97 |
| KR | 10-2007-0028512 A | 3/2007 | | A61K 6/04 |
| KR | 10-0827182 | 4/2008 | | A61K 8/19 |
| KR | 10-2008-0053406 A | 6/2008 | | A61K 8/84 |
| KR | 10-2009-0076441 | 7/2009 | | A61K 8/60 |
| KR | 10-2009-0121752 | 11/2009 | | A61K 8/33 |
| KR | 10-2011-0067358 A | 6/2011 | | A61K 6/097 |
| KR | 10-1272225 B1 | 6/2013 | | A61K 8/65 |
| KR | 10-2013-0107397 A | 10/2013 | | A61K 8/84 |
| RU | 2233651 C2 | 8/2004 | | |
| RU | 2275946 C2 | 5/2006 | | |
| UA | 85811 C2 | 2/2009 | | |
| UA | 50689 U | 6/2010 | | |
| UA | 91945 C2 | 9/2010 | | |
| UA | 95134 C2 | 7/2011 | | |
| UA | 75461 U | 12/2012 | | |
| WO | WO-01/54657 A1 | 8/2001 | | |
| WO | WO-03/045344 A2 | 6/2003 | | |
| WO | 2004032674 A1 | 4/2004 | | |
| WO | WO 2004-032889 A1 | 4/2004 | | A61K 7/16 |
| WO | WO 2006-089028 | 8/2006 | | A61K 8/20 |
| WO | WO-2009/014472 A2 | 1/2009 | | |
| WO | WO-2010/068474 A2 | 6/2010 | | |

\* cited by examiner

TOOTHPASTE EJECTION TABLE FOR DETERMINATION OF SHAPE RETENTIVITY

| | EX. 23 | | EX. 24 | | EX. 25 | | EX. 26 | | EX. 27 | | EX. 28 | | EX. 29 |

| | COMP. EX. 9 | | COMP. EX. 10 | | COMP. EX. 11 | | COMP. EX. 12 | | COMP. EX. 13 | | COMP. EX. 14 |

| | ITEM | MARK FROM POINT 5 TO POINT 1 IN ORDER OF SATISFACTION LEVEL FOR EACH QUESTION ITEM |
|---|---|---|
| 1 | SATISFACTION LEVEL OF CONVENIENCE OF USE (EJECTABILITY) OF CONTAINER | 1········2········3········4········5 |
| 2 | SATISFACTION LEVEL OF APPEARANCE QUALITY OF TOOTHPASTE | 1········2········3········4········5 |
| 3 | SATISFACTION LEVEL OF TOOTHPASTE RELEASABILITY | 1········2········3········4········5 |
| 4 | SATISFACTION LEVEL OF CLEANING QUALITY | 1········2········3········4········5 |
| 5 | OVERALL SATISFACTION LEVEL | 1········2········3········4········5 |

FIG. 5

ORAL COMPOSITION

CROSS-REFERENCE TO RELATED APPLICATIONS

This application is a national phase application of PCT Application No. PCT/KR2014/005384, filed on 18 Jun. 2014, which claims benefit of Korean Patent Application Nos. 10-2013-0124515 filed 18 Oct. 2013; 10-2013-0121432 filed 11 Oct. 2013; 10-2013-0121417 filed on 11 Oct. 2013; 10-2013-0121408 filed 11 Oct. 2013; 10-2013-0121397 filed 11 Oct. 2013; 10-2013-0069584 filed 18 Jun. 2013; 10-2013-0069583 filed 18 Jun. 2013; 10-2013-0069582 filed 18 Jun. 2013 and 10-2013-0069581 filed 18 Jun. 2013. The entire disclosures of the applications identified in this paragraph are incorporated herein by references.

FIELD

The present disclosure relates to an oral composition and a product including the same. More particularly, the present disclosure relates to a pumping type product including an oral composition, particularly a toothpaste composition, a gel-like toothpaste composition having excellent viscosity retentivity and an oral composition having excellent shape retentivity.

BACKGROUND

In the case of paste-like toothpaste used most frequently among all types of toothpastes, it has high dispersion stability and is favorable to formulation of various pharmaceutically effective ingredients. In addition, it has high shape retentivity and is favorable to maintenance of its shape after disposing toothpaste from the container thereof. However, such paste-like toothpaste has insufficient flowability due to high viscosity or the like, requires a large extent of force during its ejection from a tube to show inconvenience of use, and has low releasability to show a bad feeling of use.

Meanwhile, in the case of the conventional liquid toothpaste, it has excellent releasability but shows poor dispersion stability, and thus is limited in formulation of pharmaceutically effective ingredients. Moreover, in the case of such conventional liquid toothpaste, phase separation occurs during its distribution or use, resulting in loss of commodity value. In addition, it has insufficient shape retentivity, cannot retain a predetermined shape after disposing toothpaste onto a toothbrush, and infiltrates to the gap in the toothbrush, resulting in inconvenience of use.

Korean Patent Application No. 2001-7004081 discloses a liquid tooth washing gel having a controlled ratio of water to a wetting agent. However, the liquid tooth washing gel has problems related with shape retentivity and flowability. In addition, Korean Patent Application No. 2002-0053430 discloses improvement of shape retentivity and flowability using sodium caseinate, but the degree of improvement is insufficient to provide convenience of use to the users and sodium caseinate causes degradation of quality in terms of sensibility. Moreover, in the case of the conventional high-viscosity paste type toothpaste or liquid toothpaste, it is impossible to apply such toothpastes to various types of containers. In the case of the high-viscosity paste type toothpaste, it is difficult to eject the toothpaste when using a dip tube type pump and the toothpaste undergoes an increase in viscosity more with the lapse of time, leading to a failure in ejection. In the case of the conventional liquid toothpaste, it is not possible for the toothpaste to retain its shape even if it is ejected, leading to a failure in use.

The paste-like toothpaste that was developed first by Colgate Co. (USA) is sold in the form of an aluminum tube containing it. Even in 1970s', such an aluminum tube was still used. Improvement from such a container for paste-like toothpaste to a currently used container made of an aluminum laminate film is made by the development of polymer and polymer processing technology. However, in the case of such a tube type toothpaste, there is a lot of inconvenience of use actually due to the residual amount upon the ejection from a tube and high viscosity of a paste-like product. Then, in order to enhance convenience of use, there has been an attempt to use a vacuum pump type plastic container so that highly viscous paste may be ejected from the container. A part of such products are on sale, but they have problems in terms of cost efficiency and low releasability of the conventional paste-like toothpaste.

In general, sorbitol has been used as a wetting agent and moisturizer for paste formulations.

In the case of sorbitol, it is used in the form of 70% solution. However, such solution may be transformed into a solid undesirably after water is dried. For this reason, there has been an attempt to provide the users with enhanced convenience of use by using a dispenser pump (dip pump) applied to shampoo or body wash. However, in the case of a dispenser pump, the internal contents may be dried due to free communication with the external air when viewed from the characteristics of the container, thereby causing an increase in viscosity and a failure in ejection. The internal contents may be even solidified, and thus commercialization is limited severely.

Additionally, in the case of a toothpaste formulation, the polishing agent contained in the toothpaste has a Mohs hardness of about 3-6, which is higher than the hardness of low density polyethylene forming the piston of a dispenser pump. Therefore, there is a problem in that the piston is worn by the polishing agent contained in the toothpaste, thereby making it difficult to eject the toothpaste. For this reason, there has been a need for preparing a toothpaste composition that provides high convenience of use like shampoo and body wash by using a dispenser pump, and can be used without malfunction of a pump caused by wearing of a pump and solidification of internal contents.

Further, three has been a need for developing a toothpaste composition that solves the problem of sensational displeasure as well as the problem of solidification, while allowing application to a dip pump.

Meanwhile, according to the related art, a liquid toothpaste product having flowability in a plastic container has been launched to improve releasability of toothpaste. However, such a product flows on a toothbrush and has a difficulty in transferring the active ingredients of the toothpaste product to teeth and gum effectively. Moreover, such a liquid toothpaste product may be dried as it is in contact with the air repeatedly, resulting in the problem of an increase in viscosity.

The liquid toothpaste according to the related art causes solidification of internal contents as the viscosity increases, and cannot retain its original form to cause inconvenience of use.

Therefore, active studies have been conducted to prevent solidification of internal contents while maintaining convenience of use of the conventional liquid toothpaste.

DISCLOSURE

Technical Problem

The present disclosure is designed to solve the problems of the related art, and therefore the present disclosure is directed to providing a toothpaste composition applicable to a pumping type (dispenser pump) container and a pumping type toothpaste product including the toothpaste composition.

Particularly, the present disclosure is directed to providing a toothpaste composition that causes a reduced degree of wearing of a piston in a pumping type container and a toothpaste product including the same.

In addition, the present disclosure is directed to providing a toothpaste composition that can be used without solidification caused by a change in viscosity to provide improved convenience of use.

In addition, the present disclosure is directed to providing a gel type toothpaste composition capable of solving the above-mentioned problems and having excellent viscosity retentivity.

In addition, the present disclosure is directed to providing a toothpaste composition that can be pumped even in a container such as a dip pump without a rapid increase in viscosity and solidification despite the use of a sugar alcohol and can alleviate a bitter taste in terms of sensibility.

In addition, the present disclosure is directed to providing an oral care composition having high shape retentivity and improved flowability and dispersion stability.

Further, the present disclosure is directed to providing an oral composition that has elasticity even at low viscosity, shows little change in viscosity with time, has significantly improved shape retentivity, flowability and dispersion stability, and thus can be applied to various containers and uses.

Technical Solution

In one aspect of the present disclosure, there is provided a pumping type toothpaste product including a toothpaste composition, wherein the composition includes a lubricant.

To solve the above mentioned problems, there is provided a pumping type toothpaste product including a lubricant and polishing agent. Preferably, there is provided a pumping type toothpaste product including a polishing agent and using a lubricant in combination to prevent a piston from wearing caused by the polishing agent, and thus providing convenience of use.

As used herein, the term 'pumping type or dispenser pump' is referred to as a structure capable of ejecting the contents stored in a container through an ejection port by way of pumping action using the pushing portion of the container. Particularly, the term means a structure with which the toothpaste composition present in the container is ejected out of the container through the pumping action of the piston. In other words, the contents may be discharged from the bottom of the inner part of the container to the exterior thereof by the piston mounted to the inside of the container through pumping action.

Meanwhile, in general, the piston may be worn by the polishing agent contained in a toothpaste composition so that the contents may not be ejected smoothly. Thus, application of such a toothpaste composition using a pumping type container is limited although it is convenient to use.

Therefore, the inventors of the present disclosure have conducted many studies to obtain a pumping type toothpaste product which prevents the wearing of a piston caused by a polishing agent, prevents solidification of contents caused by the contact with the external air, and is convenient to use. The present disclosure is finished from the studies.

The toothpaste composition disclosed herein may include a polishing agent. The polishing agent contained in the toothpaste composition is a material functioning to remove dental plaque, is essentially used to increase the removal efficiency of dental plaque and to remove hard foreign materials, and has a Mohs hardness of about 3-6.

The polishing agent is present in an amount of 0.1-30 wt %, preferably 0.5-20 wt %, based on the total weight of the toothpaste composition of the toothpaste product containing the same. When the amount of the polishing agent is less than 0.1 wt %, it is difficult for the toothpaste to provide a polishing effect, resulting in poor plaque cleaning quality. When the amount of the polishing agent is larger than 30 wt %, excessive wearing of a piston may occur and a pump can hardly realize its performance.

The polishing agent may include any one selected from the group consisting of calcium monohydrogen phosphate, precipitated silica, fumed silica, colloidal silica, zeolite, calcium carbonate, hydrous alumina, kaolin, cellulose and a mixture thereof.

A polishing agent is generally used in a toothpaste composition to remove dental plaque or the like. When a toothpaste composition is provided in a pumping type product, wearing of a piston may occur due to the hardness of the polishing agent. Such a problem occurs because the piston is made of low density polyethylene and the hardness of polyethylene is lower than the hardness of the polishing agent used in the product.

The lubricant means a material with which the friction between two sliding surfaces contacting with each other is decreased. As used herein, the lubricant provides a lubricating function and thus prevents wearing of a piston caused by a material (solid content such as a polishing agent) having wearing property and contained in the toothpaste composition disclosed herein.

Particularly, petroleum-based oil, animal or vegetable oil, synthetic oil etc. may be used as liquid lubricant. More particularly, a liquid polyol may be used in view of the stability and good feeling of use of a composition.

The liquid polyol means a polyol present as liquid at room temperature, while not showing wetting property upon dissolution into water like sugar alcohol.

The lubricant may be present in an amount of 30-85 wt %, particularly 40-75 wt % based on the total weight of the toothpaste composition disclosed herein.

When the amount of the lubricant is less than 30 wt %, the toothpaste composition may be solidified with ease, the polishing agent may cause damage on a piston and the contents cannot be ejected to the exterior smoothly, and the lubricant may impart a stiff feeling of use and cause inconvenience of use. On the other hand, when the amount of the lubricant is larger than 85 wt %, the proportion of liquid ingredients in the total toothpaste composition is too low to show viscosity, and thus the toothpaste composition may flow undesirably like the conventional liquid toothpaste.

The lubricant may include any one selected from the group consisting of polyethylene glycol, glycerol, propylene glycol, ethylene glycol, polypropylene glycol and a mixture thereof. Particularly, the lubricant may include any one selected from the group consisting of polyethylene glycol 200-600, glycerol, propylene glycol, ethylene glycol, polypropylene glycol and a mixture thereof. In addition, the lubricant is not limited to a liquid polyol but includes a high-molecular weight polyol that may be liquefied, commercialized and retained in a stable state although it may be present as solid at room temperature due to the intramolecular interaction of a polymer at a molecular weight higher than a predetermined level, like polyethylene glycol or polypropylene glycol in the form of a polymer.

The inventors of the present disclosure have found that when a toothpaste composition including a polishing agent is used in combination with a liquid polyol, the toothpaste composition does not cause solidification resulting from a change in viscosity and may provide a good feeling of use. The present disclosure is based on this finding.

In another aspect, there is provided a toothpaste composition including a polishing agent in combination with a liquid polyol, the toothpaste composition causing no solidification resulting from a change in viscosity and providing a good feeling of use. There is also provided a pumping type toothpaste product including the same.

As used herein, the term 'viscosity' means an extent of viscous property of a toothpaste composition. In addition, 'viscosity retentivity' means how much the viscosity of a composition upon its preparation is retained constantly after least 2 years. Particularly, viscosity retentivity means a change in viscosity of about 100-15,000 cP after at least 2 years as compared to the viscosity upon the preparation, when viscosity measurement is carried out under the conditions of 25° C., 20 rpm and 5 cycles, by using BrookField RVT spindle No. 7 or RV-5.

In still another aspect, there is provided a toothpaste composition for use in a pumping type container, the toothpaste composition including both a sugar alcohol and a liquid polyol. Particularly, there are provided a toothpaste composition wherein both the sugar alcohol and liquid polyol are used in a pumping type container so that the contents may retain predetermined viscosity and the problem of drying may be overcome, and a pumping type toothpaste product including the toothpaste composition.

The inventors of the present disclosure have found that when a toothpaste composition is in direct contact with the external air as in the case of a pumping type container, it may be solidified with ease and may not function as toothpaste. The present disclosure solves the above-mentioned problem.

Particularly, we have found that although the sugar alcohol used as a moisturizing ingredient for a toothpaste composition has a moisturizing effect, it causes easy solidification of the composition upon the evaporation of water that is in contact with the composition.

To solve the above-mentioned problem, according to the present disclosure, the sugar alcohol contained in the toothpaste composition is allowed to react with a liquid polyol to carry out encapsulation so that the liquid polyol may surround the sugar alcohol and the sugar alcohol may not be exposed.

The reason why the liquid polyol and sugar alcohol are present in an encapsulated structure is that the hydroxyl or ether groups of a liquid polyol and the hydroxyl groups of a sugar alcohol form hydrogen bonding with each other.

The inventors of the present disclosure have thought that such hydrogen bonding solves the problem related with ejection caused by solidification and a rapid change in viscosity. The present disclosure is based on this thought.

The sugar alcohol is also referred to as solid polyol or solidifying polyol and may include erythritol, arabitol, xylitol, ribitol, sorbitol, mannitol, galactitol, maltitol, lactitol or a mixture thereof. Particularly, sorbitol may be used in any form selected from sorbitol solution, amorphous sorbitol and crystalline sorbitol with no particular limitation.

The sugar alcohol may be used in an amount of 1-70 wt %, particularly 1.5-65 wt %, and more particularly 2-60 wt %, based on the total weight of the composition.

When the sugar alcohol is used in an amount less than 1 wt %, it is not possible to improve the quality in terms of sensibility despite the use of a sugar alcohol. When the sugar alcohol is used in an amount larger than 70 wt %, the toothpaste composition may be solidified undesirably.

To accomplish the objects of the present disclosure, the liquid polyol used in combination with the sugar alcohol to maintain the viscosity of a toothpaste composition constantly and to prevent solidification of the contents may be polyethylene glycol 200-600, glycerol, propylene glycol, ethylene glycol, polypropylene glycol or a mixture thereof. Particularly, the liquid polyol may be glycerol, polyethylene glycol 300 or a mixture thereof.

The liquid polyol may be used in an amount of 10-85 wt % based on the total weight of the composition. In addition, the molar ratio of the hydroxyl or ether groups of the liquid polyol forming hydrogen bonding with the hydroxyl groups of the sugar alcohol may be at least 0.2.

When the liquid polyol is used in an amount larger than 85 wt % based on the total weight, it is not possible to carry out formulation. When the liquid polyol is used in an amount less than 10 wt % or when hydrogen bonding is formed at a proportion less than 0.2, the composition disclosed herein may undergo solidification or a rapid increase in viscosity upon the application thereof to a dip pump.

When the liquid polyol has a high content ratio of hydroxyl groups to carbon but has a low molecular weight, as in the case of glycerin or propylene glycol, the sugar alcohol and liquid polyol show strong hydrogen bonding force. However, in this case, there is a problem in that reseparation and rearrangement caused by vapor pressure may occur with ease. Thus, it is possible to solve the problems of solidification of a toothpaste composition and a rapid change in viscosity within the above-defined ratio.

In addition, when the liquid polyol has a large molecular weight as in the case of polyethylene glycol, a high-molecular weight liquid polyol and the sugar alcohol participate in hydrogen bonding, resulting in encapsulation of the sugar alcohol. When the molar ratio of the hydroxyl groups of the sugar alcohol to the hydroxyl or ether groups of the liquid polyol is at least 1:0.2, it is possible to inhibit solidification or a rapid increase in viscosity.

For example, as shown in FIG. 1, this may be exemplified by sorbitol.

Sorbitol has six carbon atoms to which six hydroxyl groups are bound. When sorbitol is in contact with water, six water molecules form hydrogen bonding to one sorbitol molecule to produce crystal water. When the formed crystal water evaporates partially or totally, it shows a crystalline form and is solidified.

Therefore, according to an embodiment of the present disclosure in which a toothpaste composition is used for a dip pump, at least one hydroxyl group of the six hydroxyl groups covalently bonded to six carbon atoms contained in one sorbitol molecule is allowed to form hydrogen bonding with a liquid polyol so that solidification or a rapid increase in viscosity may be inhibited.

In addition to the polishing agent and lubricant, the toothpaste composition may further include conventional ingredients, such as a fragrance ingredient, sweetener, pharmaceutically active ingredient, pH adjusting agent, preservative, binder, bubbling agent, whitener, or the like, depending on formulation and use. The composition according to the present disclosure may include a fragrance ingredient and sweetener to meet the consumer's preference. A fragrance ingredient remains in the oral cavity and emits fragrance continuously so that a feeling of breeziness may be continued.

Particular examples of the fragrance ingredient that may be used herein include a mint such as peppermint or spearmint, wintergreen, methyl salicylate, eugenol, melon, strawberry, orange, vanillin, or the like.

In general, a fragrance ingredient may be used in an amount of 0.001-10 wt % based on the total weight of the composition.

In addition, a sweetener may be added to the composition disclosed herein to overcome the basic taste of the formulation. Such a sweetener provides a taste while it remains in the oral cavity, thereby allowing continuance of the generation of saliva.

Particular examples of the sweetener that may be used herein include saccharin, sucralose, sugar, xylitol, sorbitol, lactose, mannitol, maltitol, erythritol, aspartame, taurine, saccharin salt, D-tryptophan or a mixture thereof. Sodium saccharin is used most widely among saccharine salts. In general, such a sweetener may be used in an amount of 0.001-20 wt % based on the total weight of the composition. A pharmaceutically active ingredient is one for use in oral hygiene, and may include ingredients effective for preventing dental caries, gum diseases and plaque deposition and for whitening. Particular examples of a pharmaceutically active ingredient effective for preventing dental caries include fluoride-containing stable compounds approved as a safe material by FDA. Particular examples of the compound that may be used as a source for fluoride include sodium fluoride, sodium monofluorophosphate, tin fluoride, ammine fluoride, or the like. The fluorine content may be varied with nations. Particularly, at least one of such sources may be used to provide a fluoride concentration of 850-1500 ppm. In general, such sources are used alone or in combination. A recalcification agent may also function as an agent for preventing dental caries. Recalcification serves to regenerate and recover hydroxyapatite, one of the main ingredients forming teeth. Main ingredients of hydroxyapatite include divalent calcium cation and phosphate anion. Therefore, the recalcification agent may be a compound that contains at least one of divalent calcium ion and phosphate anion so that calcium ion and phosphate ion may be supplied at the same time and the chemical equilibrium in the oral cavity may be shifted toward the production of hydroxyapatite. Particular examples of a material that provides calcium and phosphorus may include a raw material of hydroxyapatite, calcium hydrogen phosphate, calcium chloride, casein phosphopeptide, calcium glycerophosphate, sodium dihydrogen phosphate, sodium hydrogen phosphate, trisodium phosphate, potassium dihydrogen phosphate, potassium hydrogen phosphate, tripotassium phosphate, or the like. In general, such a recalcification agent may be used in an amount of 0.001-20 wt % based on the total weight of the composition. When the amount of recalcification agent is less than 0.001 wt %, it is not possible to provide a sufficient recalcification effect. When the amount of recalcification agent is larger than 20 wt %, the resultant formulation may lose its unique properties. One of the purposes of oral hygienic products is alleviating ongoing gum diseases or preventing gum diseases through the sterilization or anti-inflammation of harmful oral microorganisms living in the oral cavity. For this purpose, a known antibacterial agent, such as isopropylmethylphenol, cyclohexidin, cetylpyridinium chloride, triclosan or xantolisol, may be used. As an anti-inflammatory agent, vitamins, enzymes, aminocaproic acid, allantoin and derivatives thereof may be used. Such a pharmaceutically active agent may be present in an amount of 0.005 wt %-5 wt %. When the pharmaceutically active agent is present in an amount less than 0.005 wt %, it is difficult to realize a pharmaceutical effect. When the pharmaceutically active agent is present in an amount larger than 5 wt %, the formulation base undergoes a change in taste. It is also possible to use hydrogen peroxide, carbamide peroxide or calcium peroxide that shows a whitening effect in addition to an effect of alleviating or preventing gum diseases. In addition, sodium pyrophosphate, acidic sodium pyrophosphate, potassium pyrophosphate or sodium metaphosphate is used to obtain an effect of inhibiting plaque deposition. In general, such a pharmaceutically active ingredient is used in an amount of 0.001-10 wt % based on the total weight of the composition. As a pH adjusting agent, phosphoric acid, sodium phosphate, citric acid, sodium citrate, fumaric acid, sodium fumarate, tartaric acid or sodium tartrate may be used. In general, the acidity of an oral composition is 5-8. As a binder, sodium carboxymethyl cellulose, carbomer, carrageenan, xanthan gum or alginate may be used alone or in combination. Such a binder is used generally in an amount of 0.1-5 wt %, particularly 0.5-3 wt %, based on the total weight of the oral composition. As a preservative, benzoic acid, methyl paraben, propyl paraben or sodium benzoate may be used. As a bubbling agent, anionic, amphoteric or non-ionic surfactant, such as sodium alkylsulfonate, sodium laurylsulfonate, alkyl sarcosinate, lauryl sarcosinate, sodium cocoyl glutamate, sodium myristoyl glutamate, cocamidopropyl betain, sucrose fatty acid ester, sorbitan fatty acid ester, polyoxyethylene-co-polyoxypropylene (Poloxamer), may be used alone or in combination.

As a brightening agent, titanium dioxide is used, suitably in an amount of 0.1-2 wt %. The toothpaste composition disclosed herein may be obtained by a method generally known to those skilled in the art.

In still another aspect, there is provided a gel-like toothpaste composition including a polishing agent and liquid polyol. Particularly, the novel gel-like toothpaste composition uses a polishing agent and liquid polyol together so that the contents may maintain predetermined viscosity and a drying phenomenon may be improved.

As used herein, the term 'gel formulation' or 'gel-like' is used as the concept different from the conventional diluted liquid toothpaste and highly viscous paste-like toothpaste. The gel formulation is one distinguished from the conventional liquid formulation and has higher tackiness and viscosity. The gel-like toothpaste disclosed herein has elasticity and shows rigidity unlike a liquid toothpaste. In addition, the gel-like toothpaste has lower viscosity than paste type toothpaste and is fluidic, and shows flowability to allow easy ejection of the contents to the exterior.

The gel formulation disclosed herein is little diluted, unlike the conventional liquid toothpaste. Thus, when the user applies the toothpaste disclosed herein to a toothbrush, the toothpaste does not flow but is positioned stably on the toothbrush, thereby providing an excellent feeling of use to the user. Particularly, the gel-like toothpaste composition disclosed herein allows the finished toothpaste product to have a viscosity of about 5,000-36,000 cps as determined by using BrookField, RVT Type, No. 7 spindle under the conditions of 25° C., 20 rpm, 5 cycles.

The types of the polishing agent and liquid polyol contained in such a gel-like toothpaste composition are not particularly limited, as long as they are used for the pumping type toothpaste product disclosed herein.

The amounts of the polishing agent and liquid polyol are the same as in the pumping type toothpaste product. Particularly, the liquid polyol may be used in an amount selected adequately within the range used in the pumping type toothpaste product, considering the easy ejectability of the contents, viscosity of the contents or phase separation of the polishing agent.

The gel-like toothpaste composition may further include conventional ingredients that may be contained in the conventional liquid toothpaste composition in addition to the polishing agent and liquid polyol. Such conventional ingredients may include a fragrance ingredient, sweetener, pharmaceutically active ingredient, pH adjusting agent, preservative, binder, bubbling agent, brightener, or the like.

In still another aspect, there is provided an oral composition provided with elasticity based on xanthan gum.

The expression 'provided with elasticity based on xanthan gum' means that xanthan gum affects the elasticity of an oral composition. The expression 'based on xanthan gum' means that xanthan gum has a main effect upon the characteristics of an oral composition, particularly upon the shape and characteristics of the oral composition disclosed herein.

In other words, there is provided an oral composition containing xanthan gum and having elasticity. Particularly, there is provided a toothpaste composition containing xanthan gum and a thickening polymer and showing elasticity even at low viscosity.

As used herein, the term 'oral composition' may include toothpaste, mouthwash, dentures cleaner, or the like. Particularly, the term 'oral composition' means a toothpaste composition.

More particularly, there is provided an oral composition, particularly a toothpaste composition, which undergoes little change in viscosity with time and has excellent shape retentivity, flowability and dispersion stability. In addition, the composition having improved shape retentivity, flowability and dispersion stability has no particular limitation in uses and containers, and thus may be applied to various types of products.

The inventors of the present disclosure have found that the presence of xanthan gum, particularly the combination of xanthan gum with a thickening polymer, provides a toothpaste composition with excellent elasticity and improved shape retentivity. The present invention is based on this finding.

Therefore, the oral composition disclosed herein is not limited in its container upon use. However, the oral composition may be applied to a pumping type container by virtue of the above-mentioned physical properties, and thus provides convenience of use.

As used herein, the term 'elasticity' means the ability of a material to return to its original shape after it has been deformed by external force and then the force has been removed, and is used in its broad concept referring to the property of a material to maintain its original shape. In other words, the term is used in its broad meaning including all properties to maintain the original shape and height after a toothpaste composition is ejected from an ejection port.

In addition, the inventors of the present disclosure have found that incorporation of xanthan gum, particularly xanthan gum and a thickening polymer to a toothpaste composition solves the problem of the conventional high-viscosity paste-like product, including lack of flowability and requirement for excessive force upon the ejection of the product from its tube. Further, we have found that it is possible to improve the problems related with dispersion stability and shape retentivity occurring in the conventional liquid toothpaste. The present disclosure is based on these findings.

Particularly, the present disclosure provides an oral composition, particularly a toothpaste composition, capable of retaining a predetermined shape even at low viscosity to solve the problems occurring in both paste type toothpaste and conventional liquid toothpaste.

As used herein, the term 'low viscosity' means about 5,000-20,000 cps as determined by using BrookField, RV-5 under the conditions of 25° C., 20 rpm, particularly by using BrookField, RV-5 under the conditions of 25° C., 20 rpm, 5 cycles.

In addition, the term 'high viscosity' means at least a viscosity not determined under the conditions of BrookField, RV-5, 25° C., 20 rpm.

The thickening polymer may include at least one selected from the group consisting of starch, carbomer, gellan gum, gelatin, guar gum, locust bean gum, alginic acid, Arabic gum, carrageenan, agar, pectin, rheogic, cellulose and derivatives thereof.

The cellulose and derivatives thereof include any one selected from the group consisting of sodium carboxymethylcellulose, hydroxymethyl cellulose, hydroxypropylmethyl cellulose, methylethyl cellulose and a mixture thereof.

The toothpaste composition disclosed herein may include xanthan gum in an amount larger than 0.5 wt % and less than 3 wt %, particularly in an amount of 1-2.8 wt %, more particularly 1.5-2.5 wt %.

When xanthan gum is used in an amount of 0.5 wt % or less, the toothpaste composition is in the form of liquid, and thus it is not possible to impart sufficient elasticity. When xanthan gum is used in an amount of 3 wt % or more, cost efficiency is degraded as compared to improvement of effect and the toothpaste composition has high viscosity, resulting in inconvenience of use.

In addition, the toothpaste composition may further include a thickening polymer in an amount of 0.05-1 wt % based on the total weight of the composition.

When the thickening polymer is used in an amount less than 0.05 wt %, it is not possible to impart sufficient elasticity. When the thickening polymer is used in an amount larger than 1 wt %, cost efficiency is degraded as compared to improvement of effect and the toothpaste composition has high viscosity, resulting in inconvenience of use.

The toothpaste composition disclosed herein may have a viscosity of 5,000-20,000 cP as determined by using BrookField, RV-5 under the conditions of 25° C., 20 rpm, and particularly a viscosity of 5,000-20,000 cP as determined by using BrookField, RV-5 under the conditions of 25° C., 20 rpm, 5 cycles.

The oral composition having the above-defined range of viscosity is found to have excellent shape retentivity when it is formed into a product. Particularly, it has been found that when the oral composition is a toothpaste composition, it has excellent shape retentivity and convenience of use. The present disclosure is based on this finding.

Particularly, when the composition is received in a container having a diameter of 0.3-1.0 cm and is ejected to an area of width 2 cm×length 1 cm in an amount of 1 g, it has an initial height of 0.15-0.55 cm and a height of 0.1-0.45 cm after 30 seconds. The inventors of the present disclosure have found that the toothpaste composition disclosed herein has the above-mentioned characteristics, shows elasticity even at a viscosity lower than the viscosity of the conventional paste-like toothpaste and undergoes a very small change in viscosity with time.

The oral composition disclosed herein may further include various ingredients in addition to xanthan gum and a thickening polymer according to its formulation. When the oral composition is toothpaste, it may further include a wetting agent, polishing agent, fragrance ingredient, sweetener, pharmaceutically active ingredient, pH adjusting agent, preservative, bubbling agent, brightening agent or the like.

The toothpaste composition disclosed herein may be obtained by a method generally known to those skilled in the art.

Advantageous Effects

The present disclosure gives the following effects.

The toothpaste composition disclosed herein uses a pumping type container and provides convenience of use.

The conventional toothpaste composition may not be applied to a pumping type container despite its good feeling of use and has the problems of solidification caused by the contact with air or a rapid change in viscosity. The present disclosure solves the above-mentioned problems.

According to the present disclosure, it is possible to improve the wearing of the piston of a pumping type container due to a polishing agent. Thus, it is possible to provide a toothpaste composition and pumping type toothpaste product capable of ejecting the contents smoothly to the exterior of the container.

Therefore, according to the present disclosure, pumping type containers that have high cost efficiency and are manufactured with ease may be applied instead of vacuum pump type containers requiring high cost. As a result, it is possible to reduce the manufacturing cost.

Particularly, according to the present disclosure, a liquid polyol having low sensational quality is combined with a sugar alcohol to provide excellent sensational quality while solving the problem of solidification of toothpaste.

In addition, the present disclosure provides a gel-like toothpaste composition having an excellent feeling of use and high viscosity retentivity.

The gel-like toothpaste composition improves the disadvantages of a liquid toothpaste composition, including solidification caused by the contact with air, a rapid change in viscosity and inconvenience of use.

Further, the oral composition disclosed herein, particularly toothpaste composition, has high elasticity even at low viscosity.

According to the present disclosure, there is provided an oral composition, particularly toothpaste composition, which causes little change in viscosity with time and has significantly improved shape retentivity, flowability and dispersion stability.

According to the present disclosure, it is possible to solve the problems of the conventional paste-like toothpaste and liquid toothpaste, and to provide an oral composition applicable to various types of containers and various uses.

In addition, there are provided an oral composition having physical properties applicable to a pumping type container, and a pumping type toothpaste product.

DESCRIPTION OF DRAWINGS

Other objects and aspects of the present disclosure will become apparent from the following descriptions of the embodiments with reference to the accompanying drawings in which:

FIG. 5 shows a questionnaire prepared to allow consumers to evaluate the toothpaste compositions.

BEST MODE

Figure 1:
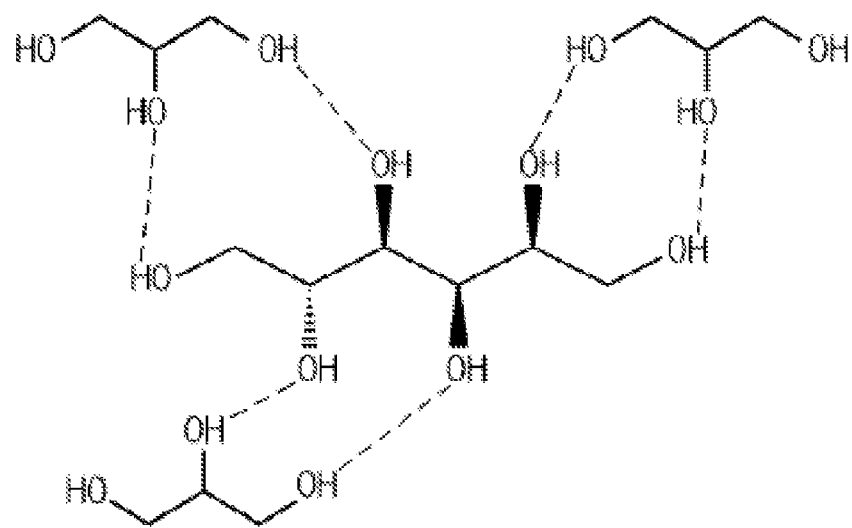
FIG. 1 is a schematic view illustrating the mechanism by which glycerin prevents direct contact between sorbitol and water.
Figure 2:
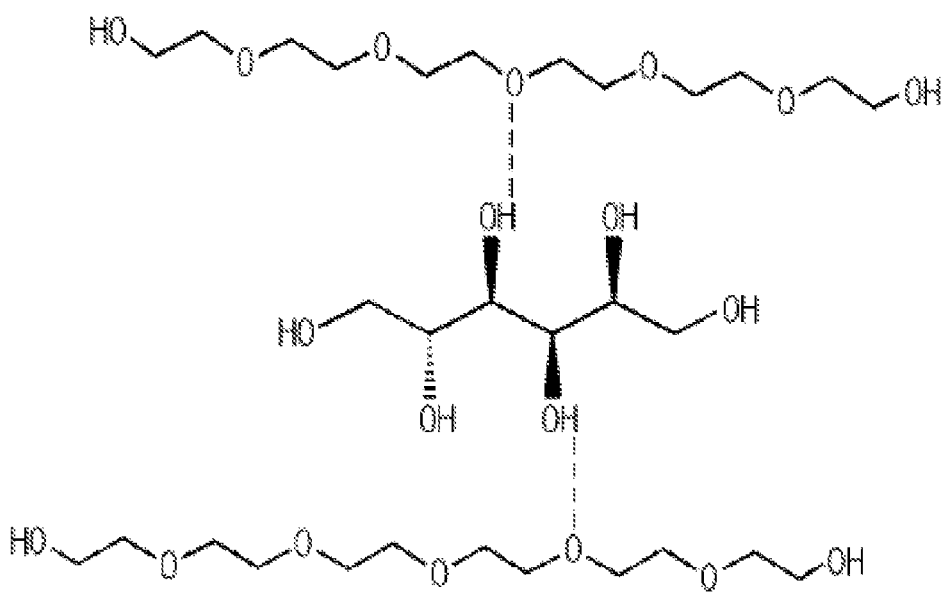
FIG. 2 is a schematic view illustrating the mechanism by which a high-molecular weight liquid polyol, polyethylene glycol 300, minimizes direct contact between a sugar alcohol and water.

Hereinafter, preferred embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just a preferable example for the purpose of illustrations only, not intended to limit the scope of the disclosure, so it should be understood that other equivalents and modifications could be made thereto without departing from the scope of the disclosure.

I. Examples 1-12 and Comparative Examples 1-4

1. Composition and Preparation

Examples 1-6 and Comparative Examples 1-2

Each of the toothpaste compositions according to Examples and Comparative Examples is obtained from the ingredients and compositions as shown in the following Table 1. Powdery ingredients including a pharmaceutically active ingredient, xanthan gum, saccharin, preservative and surfactant are dispersed completely into liquid ingredients containing purified water, glycerin and fragrance, and mixed primarily. Then, a polishing agent, such as silica, and a pharmaceutically active ingredient are introduced thereto and mixed under vacuum to obtain toothpaste compositions.

In Table 1, the amount of each ingredient is expressed in the unit of wt %.

TABLE 1

|  | Ex. 1 | Ex. 2 | Ex. 3 | Ex. 4 | Ex. 5 | Ex. 6 | Comp. Ex. 1 | Comp. Ex. 2 |
|---|---|---|---|---|---|---|---|---|
| Precipitated silica | 1.00 | 5.00 | 10.00 | 20.00 |  |  | 20.00 | 20.00 |
| Calcium carbonate |  |  |  |  | 30 |  |  |  |
| Calcium hydrogen phosphate |  |  |  |  |  | 30 |  |  |
| Glycerin | 45.00 | 45.00 | 45.00 | 45.00 | 45.00 | 45.00 | 10.00 |  |
| 70% sorbitol solution |  |  |  |  |  |  | 45.00 | 45.00 |
| Sodium laurylsulfonate | 2.00 | 2.00 | 2.00 | 2.00 | 2.00 | 2.00 | 2.00 | 2.00 |
| Sodium saccharin | 0.20 | 0.20 | 0.20 | 0.20 | 0.20 | 0.20 | 0.20 | 0.20 |
| Paraoxybenzoate | 0.15 | 0.15 | 0.15 | 0.15 | 0.15 | 0.15 | 0.15 | 0.15 |
| Xantan gum | 1.00 | 1.00 | 1.00 | 1.00 | 1.00 | 1.00 | 1.00 | 1.00 |
| Sodium fluoride | 0.22 | 0.22 | 0.22 | 0.22 |  |  | 0.22 | 0.22 |
| Sodium monofluoro phosphate |  |  |  |  | 0.76 | 0.76 |  |  |
| Vitamin E | 0.20 | 0.20 | 0.20 | 0.20 | 0.20 | 0.20 | 0.20 | 0.20 |
| Fragrance | 1.00 | 1.00 | 1.00 | 1.00 | 1.00 | 1.00 | 1.00 | 1.00 |
| Purified water | 49.23 | 45.23 | 40.23 | 30.23 | 19.69 | 19.69 | 20.23 | 30.23 |

Examples 7-12 and Comparative Examples 3-4

Each of the toothpaste compositions according to Examples and Comparative Examples is obtained from the ingredients and compositions as shown in the following Table 2. Powdery ingredients including a pharmaceutically active ingredient, xanthan gum, saccharin, preservative and surfactant are dispersed completely into liquid ingredients containing purified water, polyethylene glycol 300, glycerin and propylene glycol, and mixed primarily. Then, a polishing agent, such as silica, and a pharmaceutically active ingredient are introduced thereto and mixed under vacuum to obtain toothpaste compositions.

TABLE 2

|  | Ex. 7 | Ex. 8 | Ex. 9 | Ex. 10 | Ex. 11 | Ex. 12 | Comp. Ex. 3 | Comp. Ex. 4 |
|---|---|---|---|---|---|---|---|---|
| Precipitated silica | 15.00 | 15.00 | 15.00 | 15.00 | 15.00 | 15.00 | 20.00 | 15.00 |
| Polyethylene glycol 300 | 60.00 |  | 5 | 40 | 5 |  |  |  |
| Glycerin | — | 60.00 |  | 55 |  | 50 | 20.00 |  |
| Propylene glycol |  |  | 60.00 |  | 20 | 5 |  |  |
| Sorbitol | — |  |  |  |  |  |  | 60.00 |
| Sodium laurylsulfonate | 2.00 | 2.00 | 2.00 | 2.00 | 2.00 | 2.00 | 2.00 | 2.00 |
| Sodium saccharin | 0.20 | 0.20 | 0.20 | 0.20 | 0.20 | 0.20 | 0.20 | 0.20 |
| Paraoxybenzoate | 0.15 | 0.15 | 0.15 | 0.15 | 0.15 | 0.15 | 0.15 | 0.15 |
| Xanthan gum | 1.50 | 1.50 | 1.50 | 1.50 | 1.50 | 1.50 | 1.00 | 1.50 |
| Sodium fluoride | 0.22 | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 | 0.20 |
| Fragrance | 1.00 | 1.00 | 1.00 | 1.00 | 1.00 | 1.00 | 1.00 | 1.00 |
| Purified water | 19.73 | 19.73 | 19.73 | 19.73 | 19.73 | 19.73 | 55.23 | 19.73 |

2. Change in Viscosity with Time

The following test is carried out to observe a change in viscosity with time for each of the toothpaste compositions according to Examples and Comparative Examples listed in Table 1 and Table 2.

(1) Determination of Viscosity

Each of the toothpastes obtained according to Examples 1-12 and Comparative Examples 1-4 listed in Table 1 and Table 2 is tested right after its preparation and after 1 months and 12 months in a pumping type container by determining a change in viscosity. Determination of viscosity is carried out by using Brookfield viscometer RVT type, spindle No. 7 under a rotation speed of 10 rpm. The results are shown in the following Table 3.

TABLE 3

|  | Viscosity (X 1000 cP) | | |
|---|---|---|---|
|  | Initial time | 1 month | 12 months |
| Ex. 1 | 34 | 35 | 35 |
| Ex. 2 | 32 | 36 | 35 |
| Ex. 3 | 32 | 32 | 39 |
| Ex. 4 | 33 | 35 | 37 |
| Ex. 5 | 34 | 37 | 37 |
| Ex. 6 | 32 | 36 | 37 |
| Ex. 7 | 31 | 35 | 38 |
| Ex. 8 | 33 | 32 | 35 |
| Ex. 9 | 32 | 35 | 35 |
| Ex. 10 | 33 | 36 | 36 |
| Ex. 11 | 31 | 32 | 35 |
| Ex. 12 | 33 | 36 | 38 |
| Comp. Ex. 1 | 35 | 51 | Solidified |
| Comp. Ex. 2 | 35 | 55 | Solidified |
| Comp. Ex. 3 | 35 | 45 | 200 or more |
| Comp. Ex. 4 | 35 | 81 | Solidified |

According to Comparative Examples 1 and 2 using sorbitol, the toothpastes are solidified after the lapse of 12 months at room temperature and viscosity cannot be determined. In addition, in the case of Comparative Examples 1 and 2, a rapid change in viscosity is observed after 1 month due to the evaporation of water.

However, as can be seen from the results of Examples 1-4, no significant change in viscosity is observed even when the amount of a polishing agent increases. This suggests that the amount of a polishing agent has no significant effect upon a change in viscosity with time.

In addition, as can be seen from the results of Examples 8 and 9, incorporation of glycerin and propylene glycol causes no significant change in viscosity with time.

According to the results of Comparative Example 3, when glycerin is present in an amount of about 20 wt %, a significant change in viscosity occurs with time.

According to the results of Comparative Example 1, incorporation of both a small amount of glycerin and a solid lubricant causes a rapid increase in viscosity, and then results in solidification after the lapse of a long time. It is thought that a small amount of liquid polyol allows the toothpaste composition to maintain ejection property at the initial time but it is difficult to eject the contents as time goes by.

It can be seen from the above test results that the toothpaste composition disclosed herein undergoes little change in ejection property caused by a rapid change in viscosity, when it is applied to a dip pump.

In addition, it can be seen that the combination of a liquid polyol with a polishing agent allows the use of a dip pump even in an air permeable container without any rapid change in viscosity and solidification.

(2) Ejection from Dip Pump

Each of the toothpaste compositions according to Examples 1-12 and Comparative Examples 1-4 is received in a 250 mL pump container and pumping is carried out continuously so that the remaining amount may be 20 gram or less to evaluate the ejection property. The results are shown in the following Table 4.

TABLE 4

|  | Ejection Property | | |
|---|---|---|---|
|  | Initial time | 1 month | 12 months |
| Ex. 1 | Ejection finished | Ejection finished | Ejection finished |
| Ex. 2 | Ejection finished | Ejection finished | Ejection finished |
| Ex. 3 | Ejection finished | Ejection finished | Ejection finished |
| Ex. 4 | Ejection finished | Ejection finished | Ejection finished |
| Ex. 5 | Ejection finished | Ejection finished | Ejection finished |
| Ex. 6 | Ejection finished | Ejection finished | Ejection finished |
| Ex. 7 | Ejection finished | Ejection finished | Ejection finished |
| Ex. 8 | Ejection finished | Ejection finished | Ejection finished |
| Ex. 9 | Ejection finished | Ejection finished | Ejection finished |
| Ex. 10 | Ejection finished | Ejection finished | Ejection finished |
| Ex. 11 | Ejection finished | Ejection finished | Ejection finished |
| Ex. 12 | Ejection finished | Ejection finished | Ejection finished |
| Comp. Ex. 1 | 150 mL | 80 mL | Not ejectable |
| Comp. Ex. 2 | 200 mL | 120 mL | Not ejectable |
| Comp. Ex. 3 | 200 mL | 115 mL | Not ejectable |
| Comp. Ex. 4 | 150 mL | 80 mL | Not ejectable |

In addition, ejection property is evaluated according to the amount of sorbitol used in Comparative Examples and the amount of a polishing agent. After the evaluation, it is shown that the toothpastes according to Comparative Examples cannot be ejected any longer even at low initial viscosity, after ejecting about 150 mL. It is thought that the piston in a dip pump is worn by a polishing agent and thus complete ejection cannot be carried out. After 1 month where the viscosity increases, the ejection amount is decreases by about 50% due to the wearing of a piston caused by a polishing agent and the viscosity increases. After 1 year, the toothpastes are solidified and thus cannot be ejected any longer.

In the case of Comparative Examples 2 and 3 using glycerin in an amount of critical concentration or lower, they initially show anti-wearing property and allow sufficient ejection as compared to Examples using sorbitol alone. However, Comparative Examples 2 and 3 finally cause a rapid decrease in ejection amount due to an increase in wearing rate with time.

It can be seen from the above results that a polishing agent and a solidifying polyol lead to damages on the piston of a pump and an increase in viscosity, thereby causing a failure in ejection.

On the contrary, when using at least one selected from polyethylene glycol 300, glycerin and propylene glycol, continuous ejection is allowed with time regardless of the presence of a polishing agent. This suggests that at least one selected from polyethylene glycol 300, glycerin and propylene glycol functions as a lubricant and solves the problems of solidification, an increase in viscosity and wearing caused by a polishing agent.

II. Examples 13-22 and Comparative Examples 5-8

1. Composition and Preparation

Examples 13-17 and Comparative Examples 5-6

Each of the toothpaste compositions according to Examples and Comparative Examples is obtained from the ingredients and compositions as shown in the following Table 5. A liquid polyol is mixed with a solid polyol (or a sugar alcohol) first to induce hydrogen bonding, and then powdery ingredients including a pharmaceutically active ingredient, xanthan gum, saccharin, preservative and surfactant are dispersed completely into the solution of purified water and a fragrance ingredient, followed by further mixing. Then, if desired, a polishing agent, such as silica, and a pharmaceutically active ingredient are introduced thereto and mixed under vacuum to obtain toothpaste compositions.

In Table 5, the amount of each ingredient is expressed in the unit of wt %.

TABLE 5

|  | Ex. 13 | Ex. 14 | Ex. 15 | Ex. 16 | Ex. 17 | Comp Ex. 5 | Comp. Ex. 6 |
|---|---|---|---|---|---|---|---|
| Precipitated silica | 0.00 | 15.00 | 15.00 | 15.00 | 15.00 | 0.00 | 15.00 |
| Glycerin | 35.00 | 35.00 | 30.00 | 20.00 | 10.00 | 5.00 | 5.00 |
| 70% sorbitol solution | 45.00 | 45.00 | 45.00 | 45.00 | 45.00 | 50.00 | 50.00 |
| Sodium laurylsulfate | 2.00 | 2.00 | 2.00 | 2.00 | 2.00 | 2.00 | 2.00 |
| Sodium saccharin | 0.20 | 0.20 | 0.20 | 0.20 | 0.20 | 0.20 | 0.20 |

TABLE 5-continued

|  | Ex. 13 | Ex. 14 | Ex. 15 | Ex. 16 | Ex. 17 | Comp. Ex. 5 | Comp. Ex. 6 |
|---|---|---|---|---|---|---|---|
| Paraoxybenzoate | 0.15 | 0.15 | 0.15 | 0.15 | 0.15 | 0.15 | 0.15 |
| Xanthan gum | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 |
| Fragrance | 1.00 | 1.00 | 1.00 | 1.00 | 1.00 | 1.00 | 1.00 |
| Purified water | 15.23 | 0.23 | 5.23 | 15.23 | 25.23 | 40.23 | 25.23 |

Examples 18-22 and Comparative Examples 7-8

Each of the toothpaste compositions according to Examples and Comparative Examples is obtained from the ingredients and compositions as shown in the following Table 6. A liquid polyol is mixed with a solid or solidifying polyol first to induce hydrogen bonding, and then powdery ingredients including a pharmaceutically active ingredient, xanthan gum, saccharin, preservative and surfactant are dispersed completely into the solution of a fragrance ingredient, followed by further mixing. Then, if desired, a polishing agent, such as silica, and a pharmaceutically active ingredient are introduced thereto and mixed under vacuum to obtain toothpaste compositions.

TABLE 6

|  | Ex. 18 | Ex. 19 | Ex. 20 | Ex. 21 | Ex. 22 | Comp. Ex. 7 | Comp. Ex. 8 |
|---|---|---|---|---|---|---|---|
| Precipitated silica | 15.00 | 15.00 | 15.00 | 15.00 | 15.00 | 15.00 | 15.00 |
| Glycerin |  |  | 20.00 | 20.00 | 10.00 | 5.00 |  |
| Polyethylene glycol 300 | 20.00 |  |  |  | 10.00 |  | 5 |
| Propylene glycol |  | 20.00 |  |  |  |  |  |
| 70% sorbitol solution | 50.00 | 50.00 | 40.00 | 40.00 | 40.00 | 60.00 | 60.00 |
| Erythritol |  |  | 10.00 |  |  |  |  |
| Xylitol |  |  |  | 10.00 | 10.00 |  |  |
| Sodium laurylsulfate | 2.00 | 2.00 | 2.00 | 2.00 | 2.00 | 2.00 | 2.00 |
| Sodium saccharin | 0.20 | 0.20 | 0.20 | 0.20 | 0.20 | 0.20 | 0.20 |
| Paraoxybenzoate | 0.15 | 0.15 | 0.15 | 0.15 | 0.15 | 0.15 | 0.15 |
| Xanthan gum | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 |
| Vitamin E | 0.20 | 0.20 | 0.20 | 0.20 | 0.20 | 0.20 | 0.20 |
| Fragrance | 1.00 | 1.00 | 1.00 | 1.00 | 1.00 | 1.00 | 1.00 |
| Purified water | 10.23 | 10.23 | 10.23 | 10.23 | 10.23 | 15.23 | 15.23 |

2. Ratio of Liquid Polyol/Solid (Solidifying) Polyol in Examples and Comparative Examples The ratio of a liquid polyol to a solid polyol in each of Examples and Comparative Examples listed in Tables 5 and 6 is determined by using the ratio of the number of oxygen atoms to that of carbon atoms. For example, the number of oxygen in hydroxyl groups of glycerin is 3 per molecule. In the case of sorbitol, the number of hydroxyl groups per molecule is 6. In the case of 70% sorbitol solution, the ratio is calculated by multiplying 0.7 to obtain the oxygen mole number based on the input amount.

[Mathematical Formula 1]

$$\text{polyol equivalent ratio (liquid polyols/solid polyols)} = \frac{\sum \text{(Liquid polyol equivalent ratio ((content/molecular weight)} \times \text{purity} \times \text{number of oxygen))}}{\sum \text{(Solid polyol equivalent ratio ((content/molecular weight)} \times \text{purity} \times \text{number of oxygen))}}$$

TABLE 7

|  | Ex. 13 | Ex. 14 | Ex. 15 | Ex. 16 | Ex. 17 | Comp. Ex. 5 | Comp. Ex. 6 |
|---|---|---|---|---|---|---|---|
| Molar ratio of liquid polyol/solid polyol | 1.10 | 1.10 | 0.94 | 0.63 | 0.31 | 0.14 | 0.14 |

|  | Ex. 18 | Ex. 19 | Ex. 20 | Ex. 21 | Ex. 22 | Comp. Ex. 7 | Comp. Ex. 8 |
|---|---|---|---|---|---|---|---|
| Molar ratio of liquid polyol/solid polyol | 0.35 | 0.46 | 0.52 | 0.52 | 0.29 | 0.12 | 0.07 |

As shown in Table 7, the molar ratio of a liquid polyol/a solid polyol (a sugar alcohol) is 0.2 or more in the case of Examples, while the molar ratio is less than 0.2 in the case of Comparative Examples 5-8.

3. Change in Viscosity with Time

The following test is carried out to observe a change in viscosity with time in Examples and Comparative Examples listed in Table 5 and Table 6.

(1) Determination of Viscosity

Each of the toothpastes obtained according to Examples 13-22 and Comparative Examples 5-8 listed in Table 5 and Table 6 is tested right after its preparation and after 2 months and 12 months in a pumping type container by determining a change in viscosity. Determination of viscosity is carried out by using Brookfield viscometer (DV-III Ultra Rheometer) RVT type, spindle No. 7 under a rotation speed of 10 rpm. The results are shown in the following Table 8.

TABLE 8

|  | Viscosity (×1,000 cP) | | |
|---|---|---|---|
|  | Right after preparation | 1 month | 12 months |
| Ex. 13 | 25.6 | 34.9 | 41.5 |
| Ex. 14 | 25.1 | 32.3 | 42.8 |
| Ex. 15 | 25.6 | 31.1 | 41.0 |
| Ex. 16 | 25.2 | 34.5 | 40.2 |
| Ex. 17 | 25.7 | 31.8 | 43.5 |
| Ex. 18 | 25.4 | 33.2 | 40.1 |
| Ex. 19 | 25.8 | 32.8 | 40.6 |
| Ex. 20 | 25.3 | 33.1 | 40.2 |
| Ex. 21 | 25.5 | 33.0 | 43.1 |
| Ex. 22 | 25.9 | 34.8 | 44.0 |
| Comp. Ex. 5 | 25.2 | 54.5 | 200 or more |
| Comp. Ex. 6 | 25.5 | 54.0 | 200 or more |
| Comp. Ex. 7 | 25.5 | 53.9 | 200 or more |
| Comp. Ex. 8 | 25.8 | 54.3 | 200 or more |

When viewed from the amount of sorbitol used in Comparative Examples, the toothpastes cause solidification at their surfaces after the lapse of 12 months at room temperature, and thus viscosity itself cannot be determined. Even after 1 month, a rapid increase in viscosity is observed due to the evaporation of water. However, when the amount of a polishing agent increases, no significant change in viscosity is observed, suggesting that the amount of a polishing agent has no significant effect upon a change in viscosity with time. In addition, when a change is viscosity is observed according to type of polyol, no significant change in viscosity is observed. When a small amount of liquid polyol is used, a rapid change in viscosity is observed with time. When a small amount of liquid polyol and solid polyol are used at the same time, viscosity increases rapidly and then solidification occurs after the lapse of a long time. It is thought that a small amount of liquid polyol allows the toothpaste composition to maintain ejection property at the initial time but it is difficult to eject the contents as time goes by. It can be seen from the above test results that the toothpaste composition disclosed herein undergoes little change in ejection property caused by a rapid change in viscosity, when it is applied to a dip pump. In addition, it can be seen that the combination of a liquid polyol with a polishing agent allows the use of a dip pump even in an air permeable container without any rapid change in viscosity and solidification.

(2) Ejection from Dip Pump

Each of the toothpaste compositions according to Examples 13-22 and Comparative Examples 5-8 is received in a 250 mL dip pump container and pumping is carried out continuously so that the remaining amount may be 20 gram or less to evaluate the ejection property. The results are shown in the following Table 9.

TABLE 9

|  | Ejection property | | |
|---|---|---|---|
|  | Initial time | 1 month | 12 months |
| Ex. 13 | Ejection finished | Ejection finished | Ejection finished |
| Ex. 14 | Ejection finished | Ejection finished | Ejection finished |
| Ex. 15 | Ejection finished | Ejection finished | Ejection finished |
| Ex. 16 | Ejection finished | Ejection finished | Ejection finished |
| Ex. 17 | Ejection finished | Ejection finished | Ejection finished |
| Ex. 18 | Ejection finished | Ejection finished | Ejection finished |
| Ex. 19 | Ejection finished | Ejection finished | Ejection finished |
| Ex. 20 | Ejection finished | Ejection finished | Ejection finished |
| Ex. 21 | Ejection finished | Ejection finished | Ejection finished |
| Ex. 22 | Ejection finished | Ejection finished | Ejection finished |
| Comp. Ex. 5 | Ejection finished | 200 mL | Not ejectable |
| Comp. Ex. 6 | Ejection finished | 200 mL | Not ejectable |
| Comp. Ex. 7 | Ejection finished | 195 mL | Not ejectable |
| Comp. Ex. 8 | Ejection finished | 190 mL | Not ejectable |

In the case of Comparative Examples in which the molar ratios of hydroxyl groups of a liquid polyol/those of a solid polyol are less than 0.2, all contents are ejected right after the preparation. However, complete ejection is not allowed after 1 month, ⅕ of the contents remain in the containers, and all Comparative Examples are not ejectable after 12 months.

It can be seen that when the molar ratio of hydroxyl groups of a liquid polyol/those of a solid polyol is less than 0.2, a rapid change in viscosity and solidification occur in spite of the incorporation of a liquid polyol.

On the contrary, Examples show an increase in viscosity due to the evaporation of water but prevents solidification through the hydrogen bonding between hydroxyl groups of a liquid polyol and those of a solid polyol. According to Examples, all toothpaste compositions leave no residue after ejection. From this, it could be understood that the rapid change in viscosity upon the use of a solid polyol, which is an object to be accomplished by the present invention, is caused since water evaporates from the solid polyol and thus the solid polyol is exposed to the surface of a pump and then solidified.

III. Examples 23-29 and Comparative Examples 9-14

1. Composition and Preparation

The oral compositions (Examples 23-29) according to the present invention and the comparative conventional oral compositions (Comparative Examples 9-14) are prepared based on the compositions as shown in the following Table 10 and Table 11.

The following method is used: powdery ingredients including saccharin, a preservative and a pharmaceutically active ingredient are dispersed into wetting agents including aqueous sorbitol solution and glycerin, and the mixture is diluted with purified water and mixed primarily. Then, a polishing agent such as dental type silica and xanthan gum are introduced thereto, followed by mixing. Finally, sodium laurylsulfate as a bubbling agent and a fragrance ingredient are added and the resultant mixture is mixed under vacuum to obtain an oral composition. In Table 10 and Table 11, the amount of each ingredient is expressed in the unit of wt %.

TABLE 10

| Ingredients | Ex. 23 | Ex. 24 | Ex. 25 | Ex. 26 | Ex. 27 | Ex. 28 | Ex. 29 |
| --- | --- | --- | --- | --- | --- | --- | --- |
| Precipitated silica | 14.0 | 14.0 | 14.0 | 14.0 | 14.0 | 14.0 | 14.0 |
| Concentrated glycerin | 30.0 | 30.0 | 30.0 | 30.0 | 30.0 | 30.0 | 30.0 |
| Aqueous sorbitol solution | 30.0 | 30.0 | 30.0 | 30.0 | 30.0 | 30.0 | 30.0 |
| Sodium laurylsulfate | 1.0 | 1.0 | 1.0 | 1.0 | 1.0 | 1.0 | 1.0 |
| Sodium fluoride | 0.22 | 0.22 | 0.22 | 0.22 | 0.22 | 0.22 | 0.22 |
| Fragrance | 1.0 | 1.0 | 1.0 | 1.0 | 1.0 | 1.0 | 1.0 |
| Saccharin | 1.0 | 1.0 | 1.0 | 1.0 | 1.0 | 1.0 | 1.0 |
| Xanthan gum | 0.5 | 1.0 | 2.0 | 3.0 | 1.0 | 1.0 | 1.0 |
| Thickening polymer | 0 | 0 | 0 | 0 | Sodium carboxymethyl cellulose 0.3 | Carbomer 0.3 | Gellan gum 0.3 |
| Purified water | To100 | To100 | To100 | To 100 | To100 | To100 | To100 |

TABLE 11

| Ingredients | Comp. Ex. 9 | Comp. Ex. 10 | Comp. Ex. 11 | Comp. Ex. 12 | Comp. Ex. 13 | Comp. Ex. 14 |
| --- | --- | --- | --- | --- | --- | --- |
| Precipitated silica | 14.0 | 14.0 | 14.0 | 14.0 | 14.0 | 14.0 |
| Concentrated glycerin | 30.0 | 30.0 | 30.0 | 30.0 | 30.0 | 30.0 |
| Aqueous sorbitol solution | 30.0 | 30.0 | 30.0 | 30.0 | 30.0 | 30.0 |
| Sodium laurylsulfate | 1.0 | 1.0 | 1.0 | 1.0 | 1.0 | 1.0 |
| Sodium fluoride | 0.22 | 0.22 | 0.22 | 0.22 | 0.22 | 0.22 |
| Fragrance | 1.0 | 1.0 | 1.0 | 1.0 | 1.0 | 1.0 |
| Saccharin | 1.0 | 1.0 | 1.0 | 1.0 | 1.0 | 1.0 |
| Xanthan gum | 0.3 | 3.5 | 0 | 0 | 0 | 0 |
| Thickening polymer | 0 | 0 | 0 | Sodium carboxymethyl cellulose 0.3 | Carbomer 0.3 | Gellan gum 0.3 |
| Purified water | To100 | To 100 | To100 | To100 | To 100 | To 100 |

To determine the effects, Examples and Comparative Examples are evaluated in terms of shape retentivity, initial viscosity, a change in viscosity with time and a change in ejectability with time. Convenience of use and a feeling of use are also evaluated.

2. Test Examples

(1) Test Example 1

Evaluation of Shape Retentivity

1) Test Method

Figures 3, 4:
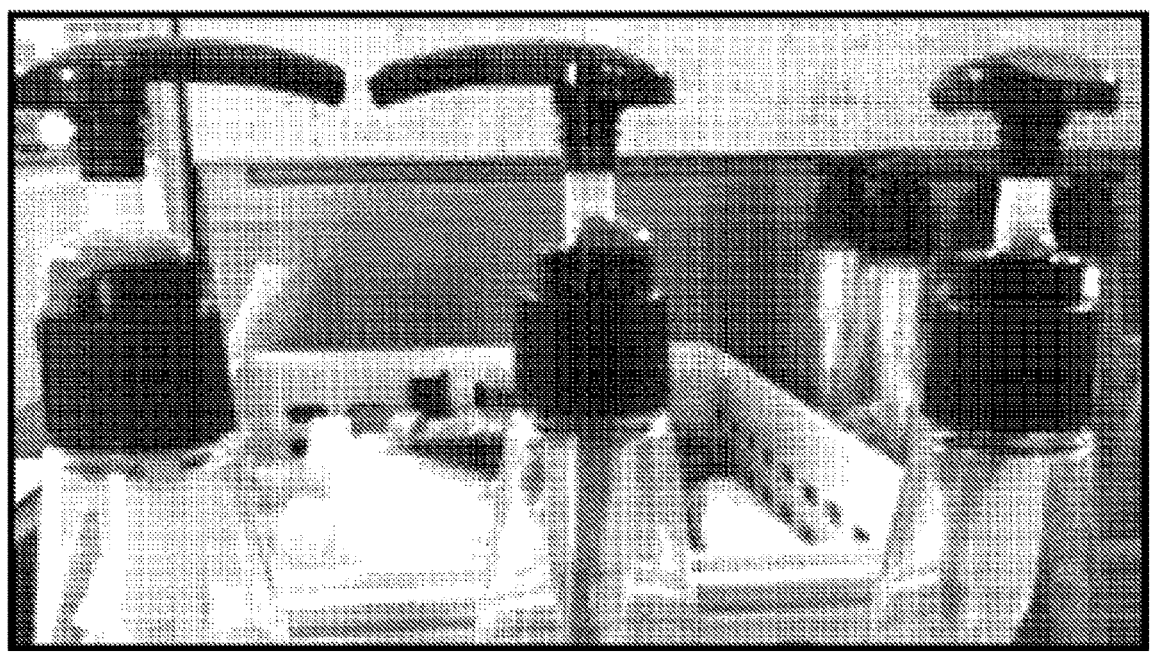
FIG. 3 is a toothpaste ejection table showing the shape retentivity of each toothpaste composition.
FIG. 4 is an image showing the pumps damaged by inadequate ejection of contents from pumping type containers.

The same amount of oral composition is taken from each of Examples and Comparative Examples and 1 g of each composition is ejected to each box of the toothpaste ejection table for determination of shape retentivity as shown in FIG. 3. The initial maximum height and the maximum height after 30 seconds are measured to evaluate shape retentivity and shape maintenance.

FIG. 3 shows a toothpaste ejection table for determination of the shape retentivity of a toothpaste composition. The table has a width of 2 cm, length of 1 cm, an interval between one box and another box of 0.5 cm, and is printed out in the form of a single page to allow ejection and observation of various compositions at the same time.

2) Test Results

As can be seen from the following Table 12, addition of xanthan gum to a composition in an amount of 0.5-3 wt % results in an increase the shape retentivity and shape maintenance of a composition. Particularly, incorporation of a thickening polymer results in a significant increase in the shape retentivity of an oral composition.

TABLE 12

Change in Height

|  | Initial height (cm) | Height after 30 seconds (cm) |
|---|---|---|
| Ex. 23 | 0.21 | 0.18 |
| Ex. 24 | 0.30 | 0.25 |
| Ex. 25 | 0.40 | 0.34 |
| Ex. 26 | 0.45 | 0.39 |
| Ex. 27 | 0.42 | 0.41 |
| Ex. 28 | 0.43 | 0.43 |
| Ex. 29 | 0.43 | 0.42 |
| Comp. Ex. 9 | 0.10 | 0.04 |
| Comp. Ex. 10 | 0.50 | 0.40 |
| Comp. Ex. 11 | 0 | 0 |
| Comp. Ex. 12 | 0.10 | 0 |
| Comp. Ex. 13 | 0.09 | 0 |
| Comp. Ex. 14 | 0.10 | 0 |

(2) Test Example 2

Determination of Change in Viscosity

1) Test Method

Each of the oral compositions according to Examples and Comparative Examples is determined for its initial viscosity right after the preparation and its viscosity after 4 weeks under the following conditions.

Conditions for determination of viscosity: BrookField, RV-5, 20 rpm, 5 cycles

2) Test Results

As can be seen from the following Table 13, addition of xanthan gum to a composition in an amount of 0.5-3 wt % results in little change in viscosity with time.

TABLE 13

Change in Viscosity

|  | Initial viscosity (cps) | Viscosity after 4 weeks (cps) |
|---|---|---|
| Ex. 23 | 5,000 | 5,200 |
| Ex. 24 | 8,000 | 8,300 |
| Ex. 25 | 11,000 | 11,100 |
| Ex. 26 | 20,000 | 20,500 |
| Ex. 27 | 11,000 | 11,200 |
| Ex. 28 | 10,800 | 11,100 |
| Ex. 29 | 11,100 | 11,300 |
| Comp. Ex. 9 | 3,000 | 3,500 |
| Comp. Ex. 10 | 25,000 | 26,000 |
| Comp. Ex. 11 | 1,000 | 1,200 |
| Comp. Ex. 12 | 2,800 | 3,000 |
| Comp. Ex. 13 | 2,600 | 2,800 |
| Comp. Ex. 14 | 3,000 | 3,100 |

(3) Test Example 3

Change in Electability with Time

1) Test Method

Each of the compositions according to Example 25 and Comparative Examples 10-14 is charged to a dip tube type pumping container and stored at 50° C. and at room temperature. The ejectability of each product is observed at the initial time, after 2 weeks and after 4 weeks.

2) Test Results

As can be seen from the following Table 14, addition of xanthan gum to a composition in an amount of 0.5-3 wt % results in excellent ejectability and pump restorability.

Particularly, in Comparative Example 9 containing 0.3 wt % of xanthan gum and Comparative Examples 11 and 12 containing no xanthan gum, the contents flounce toward different directions upon ejection due to their low viscosity. In the case of Comparative Example 10 containing 3.5 wt % of xanthan gum, the contents cannot be ejected but the pump is damaged after 4 weeks, as shown in FIG. 4.

TABLE 14

|  |  | Initial time | After 2 weeks | After 4 weeks |
|---|---|---|---|---|
| Ex. 25 | 50° C. | Ejection finished | Ejection finished | Ejection finished |
|  | Room temp. | Ejection finished | Ejection finished | Ejection finished |
| Comp. Ex. 9 | 50° C. | Ejection finished/ Contents flounce | Ejection finished/ Contents flounce | Ejection finished/ Contents flounce |
|  | Room temp. | Ejection finished/ Contents flounce | Ejection finished/ Contents flounce | Ejection finished/ Contents flounce |
| Comp. Ex. 10 | 50° C. | Ejection finished | Hardly ejected | Not ejectable |
|  | Room temp. | Ejection finished | Hardly ejected | Not ejectable |
| Comp. Ex. 11 | 50° C. | Ejection finished/ Contents flounce | Ejection finished/ Contents flounce | Ejection finished/ Contents flounce |
|  | Room temp. | Ejection finished/ Contents flounce | Ejection finished/ Contents flounce | Ejection finished/ Contents flounce |
| Comp. Ex. 12 | 50° C. | Ejection finished/ Contents flounce | Ejection finished/ Contents flounce | Ejection finished/ Contents flounce |
|  | Room temp. | Ejection finished/ Contents flounce | Ejection finished/ Contents flounce | Ejection finished/ Contents flounce |

(4) Test Example 4

Comparison of Feeling of Use and Convenience of Use Through Consumers' Evaluation 1) Test Panels Thirty test panels are recruited from male and female adult volunteers in their twenties and thirties.

2) Test Method

A new paste is supplied to the test panels weekly and the test panels are allowed to use the corresponding toothpaste only. Then, questionnaire is carried out to evaluate a feeling of use and convenience of use.

3) Toothpaste for Test

Each of the compositions according to Example 25 and Comparative Examples 9-12 is received in a dip tube type pump container and is supplied to the test panels as toothpaste for the test. All compositions have the same fragrance and color to prevent the likes and dislikes of the test panels based on a fragrance or color in advance.

4) Question Items

Evaluation is carried out by using the questionnaire for consumers' evaluation as shown in FIG. 5.

5) Test Results

Figure 6:
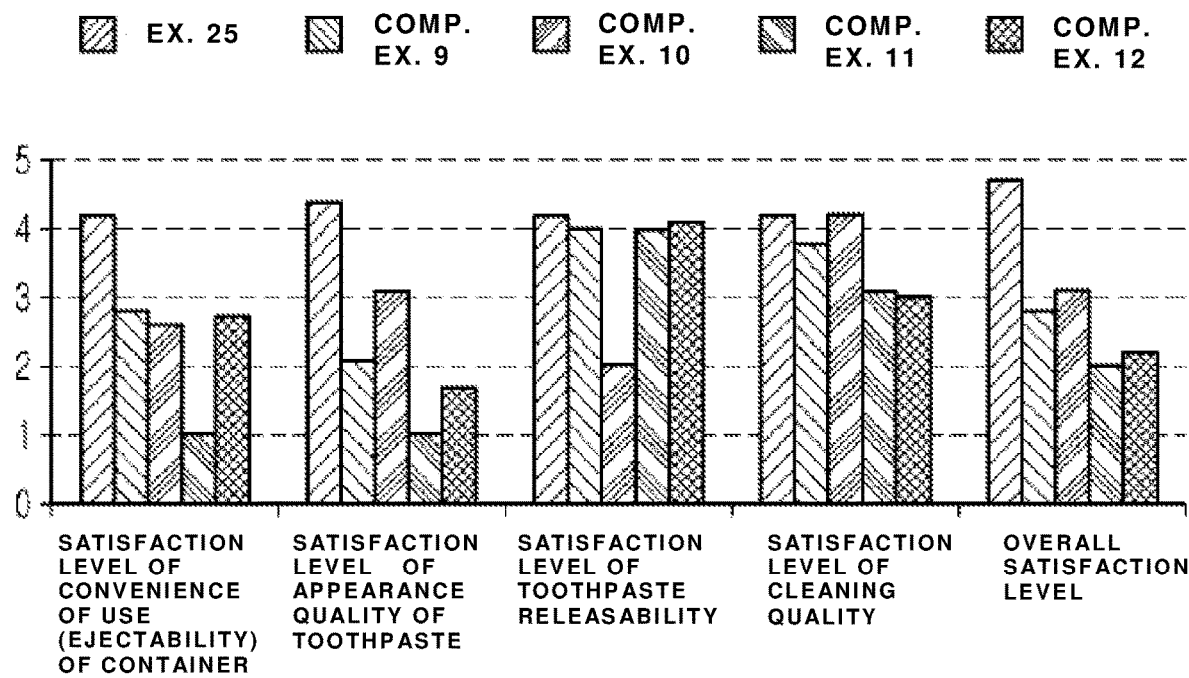
FIG. 6 is a diagram illustrating the evaluation results for toothpaste compositions after the evaluation of consumers.

After carrying out the test, it can be seen that the composition according to Example 25 provides the best results in terms of convenience of use (ejectability), appearance of toothpaste, releasability of toothpaste, cleaning quality and overall satisfaction level, as shown in FIG. 6.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A pump dispenser toothpaste product comprising:
a pump container having a piston and
a toothpaste composition for use with the pump container having a piston;
wherein the toothpaste composition comprises sorbitol, a liquid polyol, and a precipitated silica as polishing agent;
wherein the sorbitol is present in an amount of 0.001-20 wt % based on the total weight of the toothpaste composition,
wherein liquid polyol comprises any one selected from the group consisting of polyethylene glycol (PEG) 200-600, glycerol, propylene glycol, ethylene glycol, polypropylene glycol and a mixture thereof,
wherein the liquid polyol is present in an amount of 30-85 wt % based on the total weight of the toothpaste composition,
wherein the precipitated silica is present in an amount of 1-20 wt % based on the total weight of the toothpaste composition,
wherein the mole number of the hydroxyl or ether groups of the liquid polyol forming hydrogen bonding with the hydroxyl groups of the sorbitol is at least 0.2 times of the hydroxyl groups of the sorbitol,
wherein the pump container having piston comprise a dip pump, and
wherein the toothpaste composition has a change in viscosity of 100 to 15,000 cP after least 2 years as compared to the viscosity of the composition upon its preparation, when viscosity measurement is carried out under conditions of 25° C., 20 rpm and 5 cycle by using BrookField, RVT spindle No. 7.

2. The pump dispenser toothpaste product according to claim 1, wherein the liquid polyol is present in an amount of 40-75 wt % based on the total weight of the toothpaste composition.

3. The pump dispenser toothpaste product according to claim 1, wherein the toothpaste composition further comprises any one selected from the group consisting of sodium fluoride, sodium monofluorophosphate, tin fluoride, ammine fluoride and a mixture thereof.

4. The pump dispenser toothpaste product according to claim 1, wherein the toothpaste composition further comprises a bubbling agent,
wherein the bubbling agent is a laurylsulfonate.

5. The pump dispenser toothpaste product according to claim 4, wherein the bubbling agent is present in an amount of 0.5-5 wt % based on the total weight of the toothpaste composition.

6. The pump dispenser toothpaste product according to claim 1, wherein the toothpaste composition has a viscosity of 5,000-36,000 cP under conditions of 25° C., BrookField, RV-7, 20 rpm.

7. The pump dispenser toothpaste product according to claim 1, wherein the toothpaste composition has a viscosity of 5,000-20,000 cP under conditions of 25° C., Brookfield, RV-7, 20 rpm.

* * * * *